US006984518B2

(12) United States Patent
Chiu

(10) Patent No.: US 6,984,518 B2
(45) Date of Patent: Jan. 10, 2006

(54) DNA CONSTRUCT COMPRISING AN FGF1B PROMOTER REGION OPERABLY LINKED TO AN SV40 LARGE T ANTIGEN ENCODING SEQUENCE

(76) Inventor: Ing-Ming Chiu, 8664 Finlarig Dr., Dublin, OH (US) 43017

( * ) Notice: Subject to any disclaimer, the term of this patent is extended or adjusted under 35 U.S.C. 154(b) by 122 days.

(21) Appl. No.: 09/990,249

(22) Filed: Nov. 21, 2001

(65) Prior Publication Data

US 2002/0104114 A1 Aug. 1, 2002

Related U.S. Application Data

(60) Provisional application No. 60/252,745, filed on Nov. 22, 2000.

(51) Int. Cl.
C12N 15/00 (2006.01)
C07H 21/04 (2006.01)

(52) U.S. Cl. .............................. 435/320.1; 536/23.72; 536/24.1

(58) Field of Classification Search ................ 536/24.1, 536/23.72, 23.1; 435/320.1
See application file for complete search history.

(56) References Cited

PUBLICATIONS

Ausubel et al. Short Protocols in Molecular Biology. 3rd edition 1992, p. 9–28—9–30, John Wiley and Sons.*
Perraud et al. Oncogene vol. 7:993–997, 1992. Abstract Only.*
Takahashi et al. Exp. Anim. 48:255–261, 1999.*
"Multiple Controlling Mechanisms of FGF1 Gene Expression through Multiple Tissue–Specific Promoters" by Chiu, et al., *Progress for Nucleic Acid Research and Molecular Biology*, vol. 70, Oct., 2001, pp., 155–174.
"Neural stem cells isolated from adult FIB–Tag transgenic mice, which contain the FGF1B promoter and SV40 T antigen" by Chiu, et al., Keystone Symposia on Stem Cells: Origins, Fates and Functions, Mar. 17–23, 2002.
"Gene structure and differential expression of acidic fibroblast growth factor mRNA: identification and distribution of four different transcripts" by Myers, et al., *Oncogene*, (1993) 8, 341–349.
"Functional Characterization of the Brain–specific FGF–1 Promoter, FGF–1.B" by Myers, et al., *The Journal of Biological Chemistry*, vol. 270, No. 14, pp. 8257–8266, Apr. 7, 1995.
"Characterization of the 1B Promoter of Fibroblast Growth Factor 1 and Its Expression in the Adult and Developing Mouse Brain" by Alam, et al., *The Journal of Biological Chemistry*, vol. 271, No. 47, pp. 30263–30271, Nov. 22, 1996.

"Transcriptional Activation of Fibroblast Growth Factor 1.B Promoter is Mediated through and 18–Base Pair cis–Acting Element" by Ray, et al., *The Journal of Biological Chemistry*, vol. 272, No. 11, pp. 7546–7555, Mar. 14, 1997.
"A Splice Variant of E2–2 Basic Helix–Loop–Helix Protein Represses the Brain–specific Fibroblast Growth Factor 1 Promoter through the Binding to and Imperfect E–Box" by Liu, et al., *The Journal of Biological Chemistry*, vol. 273, No. 30, pp. 19269–19276, Jul. 24, 1998.
"Characterization of the Entire Transcription Unit of the Mouse Fibroblast Growth Factor 1 (FGF–1) Gene" by Madiai, et al., *The Journal of Biological Chemistry*, vol. 0274, No. 17, pp. 11937–11944, Apr. 23, 1999.
"Tumorigenesis is transgenic mice in which the SV40 T antigen is driven by the brain–specific FGF1 promoter" by Chiu, et al., *Oncogene*, (2000) 19, 6229–6239.
"Plurpotency of adult neural stem cells isolated from F1B–Tag mice, which contain the FGF1 promoter and SV40 T antigen" by Chiu, et al., U.S.—Taiwan Neuroscience Symposium, Nov. 10, 2001.

* cited by examiner

*Primary Examiner*—Deborah Crouch
(74) *Attorney, Agent, or Firm*—Calfee Halter & Griswold LLP

(57) ABSTRACT

A transgenic, non-human mammal useful for assessing the effect of candidate chemotherapeutic drugs on the growth of brain tumors in vivo is provided. Incorporated into the genome of the transgenic mammal, which preferably is a rodent, is a transgene which comprises a promoter comprising the nuclear factor binding region of the RR2 cis acting element of a fibroblast growth factor 1B (FGF1B) promoter. Operably linked to the promoter is reporter gene comprising a sequence which encodes the SV40 large T antigen. A transgenic, non-human mammal useful for identifying and isolating FGF1 producing brain cells. Incorporated into the genome of these transgenic animals is a transgene which comprises a promoter comprising the nuclear factor binding region of the RR2 cis acting element of an fibroblast growth factor 1B (FGF1B) promoter. Operably linked to the promoter is reporter gene comprising a sequence which encodes a protein or polypeptide other than an SV40 large T antigen. A method of obtaining neural stem cells from a sample of cells obtained from an animal is also provided. Such method comprises introducing the FGF1B-detector transgene into a sample of cells that have been obtained from the animal, and assaying for expression of the detectable marker in the cells, wherein cells that express the marker are neural stem cells. The cells which express the detectable marker can then be isolated from the population to provide a sub-population of neural stem cells.

6 Claims, 11 Drawing Sheets

Fig. 10A

F1B(-540)Tag plasmid, containing SV40 T/t antigen
driven by the FGF-1B (-540 to +31) promoter.

F1B540T.seq=
c:\user\xiaoqing\sequence\plasmid\psx8-34.seq
(1,592)
+ SV40.seq(5173,2536) complement of SV40 T/t Ag
+ pGL2B.seq(2741,5597) from BamHI to end.
created by i-mc on 08/01/97

^^

```
CCCGGGAGGTCCCTTTCATCCAGCAGCCTTCTGACTCCAGAGGAGAGTCTCCGAGCCACGACCTGCTGTTTCCCTGGC
AACTCAGGCCTCAAAATAAACAGGATTCTGCTCAGACGGGCCAGAAGTCCATTCGGCTCACACATTTGCCCCAAGACA
AACCACGTTAAAATAACACCCAGGGTAGCTGCTGCCACCGTCTTCTGTCTCTACCTCCCTCCTGGCTGGCCAATGGCT
CTGTGTTCCTGGGCCTGCTGCTGGCTGTCCAGAGTAGGGGTTGCTTAGAGCTGTGTGCATCCCTGCGGGTGGTGTGGG
AGTGGGCGGTTGTCTAAAGGCAGGTCCCCTCTACTGATAAACAAGGACCGGAGATAGACCTAGAGGCTGACATTCTTG
GCTCCCCCAGCCTACACCCCCCCCACCTCGATTTCCCACAGAGCCCTAGGGACGGGTAGCCAGCTCTGTGGCATGGTA
TCTGGAGGCAGGCCAGCAACCTGATGTGCATGCCACGGCCCGTCCCTCTCCCCACTCAGAGCTGCAGTAGCCTGGAGG
TTCAGAGAGCCGGGCTACTCTGAGAAGAAGACACGATCTAAGTAAGCTTTGCAAAGATGGATAAAGTTTTAAACAGAG
AGGAATCTTTGCAGCTAATGGACCTTCTAGGTCTTGAAAGGAGTGCCTGGGGAATATTCCTCTGATGAGAAAGGCAT
ATTTAAAAAAATGCAAGGAGTTTCATCCTGATAAAGGAGGAGATGAAGAAAAATGAAGAAAATGAATACTCTGTACA
AGAAAATGGAAGATGGAGTAAAATATGCTCATCAACCTGACTTTGGAGGCTTCTGGGATGCAACTGAGGTATTTGCTT
CTTCCTTAAATCCTGGTGTTGATGCAATGTACTGCAAACAATGGCCTGAGTGTGCAAAGAAAATGTCTGCTAACTGCA
TATGCTTGCTGTCGTTACTGAGGATGAAGCATGAAAATAGAAAATTATACAGGAAAGATCCACTTGTGTGGGTTGATT
GCTACTGCTTCGATTGCTTTAGAATGTGGTTTGGACTTGATCTTTGTGAAGGAACCTTACTTCTGTGGTGTGACATAA
TTGGACAAACTACCTACAGAGATTTAAAGCTCTAAGGTAAATATAAAATTTTTAAGTGTATAATGTGTTAAACTACTG
ATTCTAATTGTTTGTGTATTTTAGATTCCAACCTATGGAACTGATGAATGGGAGCAGTGGTGGAATGCCTTTAATGAG
GAAAACCTGTTTTGCTCAGAAGAAATGCCATCTAGTGATGATGAGGCTACTGCTGACTCTCAACATTCTACTCCTCCA
AAAAAGAAGAGAAAGGTAGAAGACCCCAAGGACTTTCCTTCAGAATTGCTAAGTTTTTTGAGTCATGCTGTGTTTAGT
AATAGAACTCTTGCTTGCTTTGCTATTTACACCACAAAGGAAAAAGCTGCACTGCTATACAAGAAAATTATGGAAAAA
TATTCTGTAACCTTTATAAGTAGGCATAACGTTATAATCATAACATATACTGTTTTTTCTTACTCCACACAGGCATAGA
GTGTCTGCTATTAATAACTATGCTCAAAAATTGTGTACCTTTAGCTTTTTAATTTGTAAAGGGTTAATAAGGAATAT
TTGATGTATAGTGCCTTGACTAGAGATCCATTTTCTGTTATTGAGGAAAGTTTGCCAGGTGGGTTAAAGGAGCATGAT
TTTAATCCAGAAGAAGCAGAGGAAACTAAACAAGTGTCCTGGAAGCTTGTAACAGAGTATGCAATGGAAACAAAATGT
GATGATGTGTTGTTATTGCTTGGGATGTACTTGGAATTTCAGTACAGTTTTGAAATGTGTTTAAAATGTATTAAAAAA
GAACAGCCCAGCCACTATAAGTACCATGAAAAGCATTATGCAAATGCTGCTATATTTGCTGACAGCAAAAACCAAAAA
ACCATATGCCAACAGGCTGTTGATACTGTTTTAGCTAAAAAGCGGGTTGATAGCCTACAATTAACTAGAGAACAAATG
TTAACAAACAGATTTAATGATCTTTTGGATAGGATGGATATAATGTTTGGTTCTACAGGCTCTGCTGACATAGAAGAA
TGGATGGCTGGAGTTGCTTGGCTACACTGTTTGTTGCCCAAAATGGATTCAGTGGTGTATGACTTTTTAAAATGCATG
GTGTACAACATTCCTAAAAAAAGATACTGGCTGTTTAAAGGACCAATTGATAGTGGTAAAACTACATTAGCAGCTGCT
TTGCTTGAATTATGTGGGGGAAAGCTTTAAATGTTAATTTGCCCTTGGACAGGCTGAACTTTGAGCTAGGAGTAGCT
ATTGACCAGTTTTTAGTAGTTTTTGAGGATGTAAAGGGCACTGGAGGGGAGTCCAGAGATTTGCCTTCAGGTCAGGGA
ATTAATAACCTGGACAATTTAAGGGATTATTTGGATGGCAGTGTTAAGGTAAACTTAGAAAAGAAACACCTAAATAAA
AGAACTCAAATATTTCCCCCTGGAATAGTCACCATGAATGAGTACAGTGTGCCTAAAACACTGCAGGCCAGATTTGTA
AAACAAATAGATTTTAGGCCCAAAGATTATTTAAAGCATTGCCTGGAACGCAGTGAGTTTTTGTTAGAAAAGAGAATA
ATTCAAAGTGGCATTGCTTTGCTTCTTATGTTAATTTGGTACAGACCTGTGGCTGAGTTTGCTCAAAGTATTCAGAGC
AGAATTGTGGAGTGGAAAGAGAGATTGGACAAAGAGTTTAGTTTGTCAGTGTATCAAAAAATGAAGTTTAATGTGGCT
ATGGGAATTGGAGTTTTAGATTGGCTAAGAAACAGTGATGATGATGATGAAGACAGCCAGGAAAATGCTGATAAAAAT
GAAGATGGTGGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAAAA
CCTCCCACACCTCCCCCTGAACCTGAAACATAAAATGAATGCAATTGTTGTTGTTAACTTGTTTATTGCAGCTTATAA
TGGTTACAAATAAAGCAATAGCATCACAAATTTCACAAATAAAGCATTTTTTTCACTGCATTCTAGTTGTGGTTTGTC
CAAACTCATCAATGTATCTTATCATGTCTGGATCCGTCGACCGATGCCCTTGAGAGCCTTCAACCCAGTCAGCTCCTT
CCGGTGGGCGCGGGGCATGACTATCGTCGCCGCACTTATGACTGTCTTCTTTATCATGCAACTCGTAGGACAGGTGCC
GGCAGCGCTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGCAAAGG
CCAGGAACCGTAAAAAGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCAATGCT
CACGCTGTAGGTATCTCAGTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTATCGCCACTGGCAGCAGCCA
```

Fig. 10B

```
CTGGTAACAGGATTAGCAGAGCGAGGTATGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCGAGTTGCTCTTGCCCGG
CGTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCTT
TTACTTTCACCAGCGTTTCTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCACCTGACGCGCCCT
GTAGCGGCGCATTAAGCGCGGCGGGTGTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTAGGGTGATGGTTCACGTAGTGGGCCAT
CGCCCTGATAGACGGTTTTTCGCCCTTTGACGTTGGAGTCCACGTTCTTTAATAGTGGACTCTTGTTCCAAACTGGAA
CAACACTCAACCCTATCTCGGTCTATTCTTTTGATTTATAAGGGATTTTGCCGATTTCGGCCTATTGGTTAAAAAATG
AGCTGATTTAACAAAAATTTAACGCGAATTTTAACAAAATATTAACGTTTACAATTTCCCATTCGCCATTCAGGCTGC
GCAACTGTTGGGAAGGGCGATCGGTGCGGGCCTCTTCGCTATTACGCCAGCCCAAGCTACCATGATAAGTAAGTAATA
TTAAGGTACGTGGAGGTTTTACTTGCTTTAAAAAACCTCCCACACCTCCCCCTGAACCTGAAACATAAAATGAATGCA
ATTGTTGTTGTTAACTTGTTTATTGCAGCTTATAATGGTTACAAATAAAGCAATAGCATCACAAATTTCACAAATAAA
GCATTTTTTTCACTGCATTCTAGTTGTGGTTTGTCCAAACTCATCAATGTATCTTATGGTACTGTAACTGAGCTAACA
TAA
```

DNA CONSTRUCT COMPRISING AN FGF1B PROMOTER REGION OPERABLY LINKED TO AN SV40 LARGE T ANTIGEN ENCODING SEQUENCE

This application claim priority to U.S. Provisional Application Ser. No. 60/252,745 filed Nov. 22, 2000.

BACKGROUND

Animal model systems are useful tools for identifying and characterizing therapeutic agents. Examples of such model systems are transgenic animal models with brain tumors. Currently, there are several transgenic animal models that recapitulate key features of human primitive neuroectodermal tumors (PNET) (Fung, K. M., and Trojanowski, J. Q., (1995) Animal models of medulloblastomas and related primitive neuroectodermal tumors. A review. J. Neuropathol. Exp. Neurol. 54, 285–296). Members of each of these transgenic animal lines develop PNETs arising in different, yet distinct, brain regions. However, the animals in these four transgenic lines also have some features in common, namely the expression of the neuronal cell marker synaptophysin (Fung, K. M., Chikaraishi, D. M., Suri, C., Theuring, F., Messing, A., Albert, D. M., Lee, V. M., Trojanowski, J. Q. (1994). Molecular phenotype of simian virus 40 large T antigen-induced primitive neuroectodermal tumors in four different lines of transgenic mice. Lab. Invest. 70, 114124). The presence of this cell marker indicates that these tumors are derived from cells that have differentiated beyond the earliest stages of neural stem cells.

It is desirable to have additional animal models for identifying agents which are effective at preventing, slowing or reversing the growth of brain tumors. It is especially desirable to have an animal whose brain tumor cells are at an early stage of differentiation, i.e., the tumor cells have not yet progressed to the stage where they are expressing markers that are indicative of neurons (synaptophysin and neuron-specific enolase), astrocytes (glial fibrillary acidic protein and S-100), or oligodendrocytes (galactocerebroside).

SUMMARY OF THE INVENTION

The present invention provides a novel, transgenic, non-human mammal useful for assessing the effect of candidate chemotherapeutic drugs on the growth of brain tumors in vivo. Incorporated into the genome of the transgenic mammal, which preferably is a rodent, is a transgene which comprises a promoter comprising the nuclear factor binding region of the RR2 cis acting element of a fibroblast growth factor 1B (FGF1B) promoter. Operably linked to the promoter is reporter gene comprising a sequence which encodes the SV40 large T antigen. Such transgene is referred to hereinafter as the "FGF1B-T antigen" transgene. The present invention also provides a DNA construct comprising the transgene.

The present invention provides a novel, transgenic, non-human mammal useful for identifying and isolating FGF1 producing brain cells. Incorporated into the genome of these transgenic animals is a transgene which comprises a promoter comprising the nuclear factor binding region of the RR2 cis acting element of an fibroblast growth factor 1B (FGF1B) promoter. Operably linked to the promoter is reporter gene comprising a sequence which encodes a protein or polypeptide other than an SV40 large T antigen. Such protein is a detectable marker that permits identification and separation of transgenic animal brain cells that are expressing such marker from transgenic animal brain cells that are not. Such transgene is referred to herein after as the "FGF1B-detector" transgene.

In one embodiment, nuclear factor binding region of the RR2 cis acting element is derived from the human FGF1B promoter and comprises the sequence 5' ACCTGCTGTTTCCCTGGCAACTC, 3', SEQ ID NO. 1. In one embodiment, the promoter comprises nucleotide −540 through nucleotide +1 of the human FGF1B promoter. In another embodiment the promoter is a chimeric promoter which comprises SEQ ID NO. 1 and the minimal Herpes Simplex Virus (HSV) thymidine kinase (tk) promoter.

The transgenic animals whose genome comprises the FGF1B-T antigen transgene exhibit a phenotype which is different from the phenotype of normal animals of the same species. For example, these transgenic mice whose genome comprises the FGF1B-T antigen transgene develop tumor foci in the pontine gray area of the brain The brain tumor cells that are derived from mature transgenic mice (i.e., transgenic mice that are greater than 3 months old) whose genome comprises the FGF1B-T antigen transgene lack terminal differentiation markers for astrocytes (glial fibrillary acidic protein and S-100) or neurons (synaptophysin and neuron-specific enolase). The brain tumor cells of the transgenic mice whose genome comprises the FGF1B-T antigen transgene also express higher levels of proliferating cell nuclear antigen and vimentin than brain cells from normal mice at the same stage of development, indicating that the brain tumor cells of such transgenic mice are proliferative.

The present invention also provides isolated mutant non-human mammalian zygotes whose genome comprises the present transgenes. Such zygotes are useful for making the mutant non-human mammals.

The present invention further relates to isolated transformed brain cells derived from the transgenic animals whose genome comprises the FGF1B-T antigen transgene and from the transgenic animals whose genome comprises the FGF1B-detector transgene. Such brain cells are useful for identifying markers that are unique to neural stem cells. Neural stem cells are considered possible therapeutic agents for treating patients with neurodegenerative diseases such Alzheimer's disease, Parkinson's disease, stroke, and spinal cord injury.

The present invention also relates to a method of using the transgenic animals whose genome comprises the FGF1B-T antigen transgene to identify drugs which inhibit the growth of brain tumors in vivo.

The present invention also provides a method of obtaining neural stem cells from a sample of cells obtained from an animal. Such method comprises introducing the FGF1B-detector transgene into a sample of cells that have been obtained from the animal, and assaying for expression of the detectable marker in the cells, wherein cells that express the marker are neural stem cells. The cells which express the detectable marker can then be isolated from the population to provide a sub-population of neural stem cells. Preferably, the sample is a brain tissue sample.

BRIEF DESCRIPTION OF THE FIGURES

FIG. 10 is the nucleotide sequence (SEQ ID NO. 2) of the plasmid containing the transgene designated FIB(–540)-Tag. Nucleotides 1–594 are derived from the human FGF1B promoter (Accession No. Z14150 cloned in our laboratory. Nucleotides 595–3233 are derived from the reverse complement of SV40 from nucleotides 5171–2533 (Accession No. NC-001669).

Figure 1:
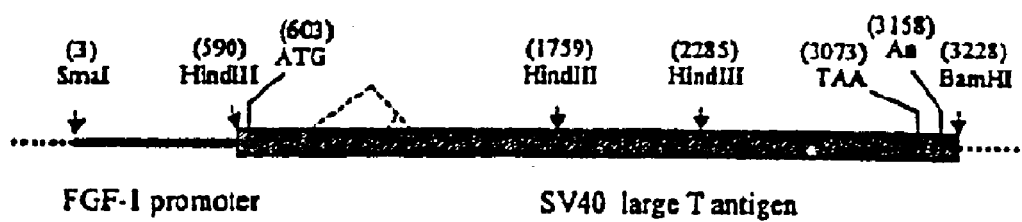
FIG. 1. Restriction map of FIB-Tag construct. The thick line represents the human FGF-1B promoter sequence. The hatched box represents the SV40 immediate early genes. Dashed lines indicate the introns for the large T and small t antigens. ATG and TAA are the translational initiation and termination codons for SV40 T antigen. The polyadenylation site is symbolized by An. Dotted lines represent the vector sequence derived from pGL2-Basic plasmid. As such, an additional copy of the SV40 polyadenylation signal sequence is located upstream from the FGF1 promoter to prevent stray transcription initiated from flanking host genomic sequences.

Nuleotides 3234–36087 are derived from nucleotides 2544–5597 of the pGL2-Basic vector (Promega Corp).

DETAILED DESCRIPTION OF THE INVENTION

In one aspect, the present invention provides a transgenic, non-human mammal useful for assessing the effect of a candidate chemotherapeutic agent on the growth of brain tumors.

Incorporated into the genome of the transgenic mammal is the FBF1B-T antigen transgene which comprises a promoter comprising an active portion of the FGF1B promoter. Operably linked to the promoter is a reporter gene, i.e., DNA fragment, comprising a sequence encoding the SV40 large T antigen. The term "active portion of the FGF1B promoter" as used herein refers to the nuclear factor binding region of the RR2 cis acting element of the FGF1B promoter. In one embodiment the active portion is derived from the human FGF1B promoter and comprises SEQ ID NO. 1.

In another aspect, the present invention provides a non-human, transgenic mammal, preferably a transgenic rodent, useful for identifying and providing FGF1 producing brain cells. In accordance with the present invention, it is expected that FGF1 producing brain cells are neural stem cells. Incorporated into the genome of these transgenic animals is the FGF1B-detector transgene which comprises a promoter comprising the nuclear factor binding region of the RR2 cis acting element of an FGF1B promoter. Operably linked to the promoter is a reporter gene comprising a sequence which encodes a protein other than an SV40 large T antigen. Such protein is a detectable marker that permits identification and isolation of transgenic animal brain cells that are expressing such marker from transgenic animal brain cells that are not.

The term "mammal" as used herein refers to any non-human mammal. Such animals are, for example, rodents, non-human primates, sheep, dogs, cows, and pigs. The preferred non-human mammals are selected from the rodent family including rat and mouse, more preferably mouse. A "transgenic mammal" as used herein refers to an animal containing one or more cells bearing genetic information, received, directly or indirectly, by deliberate genetic manipulation at the subcellular level, such as by microinjection or transfection with recombinant DNA, or infection with recombinant virus. The term "germ cell-line transgenic animal" refers to a transgenic animal in which the genetic information was introduced into a germ line cell, thereby conferring the ability to transfer the information to offspring. If such offspring in fact possess the transgene, they too are transgenic mammals.

PROMOTER

In one aspect, the promoter may comprise in order (i) the RR2 cis acting element (nucleotides −507 to −467 of the human FGF1B promoter), (ii) the RR1 cis acting element (nucleotides −145 to −114 of the human FGF1B promoter), and (iii) the proximal promoter (nucleotides −92 to −49 of the human FGF1B promoter), of a native or naturally occurring FGF1B promoter that is derived from an animal, such as for example a human, a mouse, a bovine animal, a chick or an amphibian. The sequence of the FGF1B promoter of human is provided in GenBank Accession No. Z14150, which is specifically incorporated herein by reference. The sequence of the FGF1B promoter of the mouse is provided in GenBank Accession No. U67609 (SEQ ID NO. 3), which is specifically incorporated herein by reference. The RR2 region of mouse FGF1B promoter contains a minimal sequence from nucleotide 640–679 of Accession No. U67609, based on its homology with the human FGF1B promoter and its relative location to the transcription start site of the mouse FGF1B mRNA.

In one embodiment, the promoter is derived from a human and comprises nucleotides −145 to nucleotide +1, preferably nucleotide −507 through nucleotide +1, and more preferably nucleotide −540 to nucleotide +1, which is the transcription initiation site, of the human FGF1B promoter. Preferably, the promoter which is derived from FGF1B promoter of an animal further comprises nucleotides downstream from the transcription site, such as for example the 31 nucleotides of the 5'-untranslated sequence of the corresponding FGF1 gene.

In accordance with the present invention, it has been determined that a promoter comprising 540 base pairs of the human FGF1B promoter sequence and the first 31 base pairs of the 5'-untranslated sequence of the human FGF1B mRNA is particularly well-suited for preparing the transgene.

Alternatively, the promoter is a chimeric promoter which comprises the proximal promoter of a heterologous, i.e., a non-FGF1B, promoter and the nuclear factor binding region of the RR2 cis acting element of a mammalian FGF1B promoter. The sequence that constitutes the proximal promoter provides basal level of transcriptional activity. In one embodiment, the element is derived from nucleotide −484 through nucleotide −467 of the human FGF1B promoter and comprises SEQ ID NO. 1. In one embodiment, the heterologous promoter is the full length HSV tk promoter (from nucleotides −200 to +67), the sequence of which is provided in Accession No. V00467, which is specifically incorporated herein by reference. In another embodiment, the heterologous promoter is minimal HSV tk promoter fragment which comprises nucleotide −81 through nucleotide +67 of the full-length HSV tk promoter. Examples of other heterologous promoters include, but are not limited to, the adenoviral E1b TATA promoter, the human cytomegalovirus major immediate-early gene promoter, the heat shock protein (hsp70) promoter, and the dihydrofolate reductase (dhfr) promoter.

REPORTER GENES

The transgene further comprises a reporter gene. As used herein the term "reporter gene" refers to a DNA fragment that encodes an assayable product The assayable product is a protein or peptide which permits differentiation of transformed brain cells which express such gene from cells that do not. As used herein the term "transformed" brain cell refers to a brain cell whose phenotype is different from a normal brain cell in that the transformed brain cell comprises a protein or polypeptide that is not found in the normal brain cell. In one embodiment, the reporter gene is derived from the SV40 genome and encodes the SV40 large T antigen. Preferably the SV40 DNA fragment comprises nucleotides 5163–2691, more preferably 5171–2533 of the SV40 immediate early gene which is depicted in GenBank Accession No. NC_00166.

In other embodiments, the reporter gene is not derived from the SV40 genome. Examples of such reporter genes include, but are not limited to, genes for drug and metabolite selection of transformed cells, genes that express an exogenous cell membrane protein, and genes that encode a fluorescent protein, and genes that encode a protein that can be detected by immunocytochemistry. Some examples of reporter genes that encode proteins that permit drug or metabolite selection are the gpt reporter gene, the neomycin reporter gene, the thymidine kinase reporter gene, the dhfr reporter gene, the hygromycin reporter gene, the tryptophan reporter gene and the histidine reporter gene. Expression of gpt reporter protein resistance to the HAT (hypoxanthine, aminopterin and thymidine) selection medium or to mycophenolic acid ((Mulligan R C, Berg P: Selection for animal cells that express the *Escherichia coli* gene coding for xanthine-guanine phosphoribosyl transferase. Proc. Natl. Acad. Sci. USA 78: 2072–2076, 1981). Expression of neo confers G418 resistance; while expression of tk reporter protein provides a negative selection in the presence of gangcyclovir (Mansour S L, Thomas K R, Capecchi M R. Disruption of the proto-oncogene int-2 in mouse embryo-derived stem cells: a general strategy for targeting mutations to non-selectable genes. Nature. 336: 348–352, 1988). Cells expressing dhfr are selected for increased resistance to methotrexate (Wigler M, Perucho M, Kurtz D, Dana S, Pellicer A, Axel R, Silverstein S: Transforming of mammalian cells with an amplifiable dominant-acting gene. Proc. Natl. Acad. Sci. USA 77:3567–3570, 1980). Expression of hygro provides for hygromycin B resistance (Yang Z, Korman A J, Cooper J, Pious D, Accolla R S, Mulligan R C, Strominger J L. Expression of HLA-DR antigen in human class II mutant B-cell lines by double infection with retrovirus vectors. Mol Cell Biol 7: 3923–3928, 1987). Expression of the trpB gene of *Escherichia coli*, which encodes the beta subunit of tryptophan synthase, allows mammalian cell survival and multiplication in medium containing indole in place of tryptophan (Hartman S C, Mulligan R C: Two dominant-acting selectable markers for gene transfer studies in mammalian cells. Proc. Natl. Acad. Sci. USA 85:8047–8051, 1988). The hisD gene of Salmonella typhimurium encodes histidinol dehydrogenase, which catalyzes the oxidation of L-histidinol to L-histidine. In medium lacking histidine and containing histidinol, only mammalian cells expressing the hisD product survive (Hartman S C, Mulligan R C: Two dominant-acting selectable markers for gene transfer studies in mammalian cells. Proc. Natl. Acad. Sci. USA 85:8047–8051, 1988).

Reporter genes encoding a cell membrane protein, such as CD2, can facilitate the selection of transformed brain cells by an immunoselection "panning" procedure with an antibody reacting to the expressed exogenous membrane protein (Seed B, Aruffo A. Molecular cloning of the CD2 antigen, the T-cell erythrocyte receptor, by a rapid immunoselection procedure. Proc. Natl. Acad. Sci. USA 84: 3365–3369, 1988.)

Transformed brain cells that express a fluorescent protein can be isolated using fluorescence activated cell sorter as described by Roy et al. (Roy N S, Benraiss A, Wang S, Fraser R A, Goodman R, Couldwell W T, Nedergaard M, Kawaguchi A, Okano H, Goldman S A. Promoter-targeted selection and isolation of neural progenitor cells from the adult human ventricular zone. J Neurosci Res. 59:321–331, 2000). Examples of such fluorescent protein include, but are not limited to luciferase protein (Myers, R. L., Ray, S. K., Eldridge, R., Chotani, M. A., and Chiu, I. -M. (1995). Functional characterization of the brain-specific FGF-1 promoter, FGF-1.B. J. Biol. Chem. 270, 8257–8266.) and green fluorescent protein (Heim R, Tsien R Y: Engineering green fluorescent protein for improved brightness, lower wavelengths and fluorescence resonance energy transfer. Curr. Biol. 6:178–182, 1996).

The transgene also contains a ribosome binding site for translation initiation and a transcription terminator.

In another aspect, the present invention relates to a DNA construct comprising the transgene. Such construct is an expression vector, preferably a plasmid which allows for preparation of large amounts of the transgene. In such a plasmid, the transgene is flanked by restriction sites and, preferably comprises an origin of replication. Such construct may be made by cloning the promoter sequence into a vector comprising the reporter gene sequence or by cloning the reporter gene sequence into a vector comprising the promoter sequence, using conventional recombinant techniques. The DNA sequence encoding the promoter is incorporated into the construct in appropriate frame with the reporter gene sequence such that induction of the promoter causes expression of the reporter gene.

In another aspect the present invention relates to a zygote or embryonic stem cell whose genome comprise the transgene. A DNA construct which comprises the present transgene may be integrated into the genome of the transgenic animal by any standard method such as those described in Hogan et al., "Manipulating the Mouse Embryo", Cold Spring Harbor Laboratory Press, 1986; Kraemer et al., "Genetic Manipulation of the Early Mammalian Embryo", Cold Spring harbor Laboratory Press, 1985; Wagner et al., U.S. Pat. No. 4,873,191, Krimpenfort et al U.S. Pat. No. 5,175,384 and Krimpenfort et al., Biotechnology, 9: 88 (1991), all of which are incorporated herein by reference. Preferably, the DNA fragment is microinjected into pronuclei of zygotes of non-human mammalian animals, such as mice, rabbits, cats, dogs, or larger domestic or farm animals, such as pigs. These injected embryos are transplanted to the oviduts or uteri of pseudopregnant females from which founder animals are obtained. The founder animals (Fo) founder, are transgenic (heterozygous) and can be mated with non-transgenic animals of the same species to obtain F1 non-transgenic and transgenic offspring at a ratio of 1:1. A heterozygote animal from one line of transgenic animals may be crossed with a heterozygote animal from a different line of transgenic animals to produce animals that are heterozygous at two loci. Animals whose genome comprises the transgene are identified by standard techniques such as polymerase chain reaction or Southern assays.

The heterozygote offspring in the F1 generation or F2 generation develop brain tumors whose cells possess a neural stem cell phenotype as they do not express the markers for either glial cells or neuronal cells. Accordingly, the heterozygous transgenic animals are useful tools for screening candidate agents capable of inhibiting, slowing or reversing the growth of brain tumors in a mammal. Such transgenic animals are also useful for studying tumorigenesis in the central nervous system.

Suitable embryonic stem cells are those that have the ability to integrate into and become part of the germ line of a developing embryo. Introduction of the transgene into the embryonic stem cell can be accomplished using a variety of methods well known in the art, such as for example, retrovirus-mediated transduction, microinjection, calcium phosphate treatment, or, preferably, electroporation. Thereafter, the transgene is integrated into the genome of some of the transfected cells, typically by non-homologous recombination. If the construct further comprises an antibiotic resistance gene, the transfected cells are cultured in the presence of the antibiotic. If the construct further comprises a sequence encoding an assayable enzyme, the substrate for the enzyme can be added to the cells under suitable conditions, and the cells containing the product of enzymatic activity identified. Another assay is a Southern blot of the transfected cells genomic DNA can be probed with a sequence designed to hybridize with the transgene. The mutant cells containing the transgene are used to prepare the mutant animals, typically by insertion into an embryo of the same species of animal.

In another aspect, the present invention provides a method for identifying agents which are effective at inhibiting, slowing or reversing the growth of brain tumors in a mammal. The method comprises the steps of administering the candidate agents to the transgenic animal and monitoring the growth of the tumor. Preferably, varying doses of the candidate agents are introduced into the separate transgenic mammals intracerebrally or by conventional modes of injection, such as for example, by intravenous injection or intraperitoneal injection The present invention also relates to tumor cells or tumor cell lines derived from the transgenic animal whose genome comprises the FGF1B-T antigen transgene. Such cells are obtained from the brain tumors of such transgenic animals using conventional methods known in the art. In view of their phenotype, it is expected that such cells would be useful for neural stem cell therapy for patients with neurodegenerative diseases such as Alzheimer's disease, Parkinson's disease, stroke, and spinal cord injury. Such cells would also be useful for identifying additional neural stem cell markers.

In one embodiment, the tumor cells are from the mouse brain tumor cell line KT-98, which has been deposited with the with the American Type Culture Collection, 10801 University Blvd, Manassas, Va. 201110-2209 and assigned designation number PTA-3661. The ATCC is a Budapest Treaty depository. The transgene which is incorporated into the cells of this cell line comprises nucleotides −540 to +31 of the human FGF1B promoter and the SV40 T antigen Tag.

In another aspect, the present invention comprises a method of obtaining neural stem from a sample of cells, e.g., a biopsy specimen, obtained from an animal. The cells which are isolated from the sample using standard techniques are grown in tissue culture medium The FGF1B-detector transgene is then introduced into the cultured cells, for example by transfection or electroporation with a construct containing the FGF1B-detector transgene, or infection with recombinant viruses containing the FGF1B-detector transgene. The cells that have incorporated the transgene are either expressing or not expressing the transgene. Cells that express the transgene are the FGF-1 producing cells, and therefore neural stem cells. These neural stem cells can be isolated from the population of cells in the sample using the proper detection method, either by drug/metabolite selection, fluorescence activated cell sorting, immunodetective "panning," or immunohistochemistry. These FGF1-producing neural stem cells could then be propagated for stem cell based therapy in patients with neurodegenerative diseases. In one embodiment the recipient cells for the FGF1B-detector transgene are brain cells. In another embodiment, the recipient cells for the FGF1B-detector transgene are obtained from a sample other than a brain tissue sample. The recipient cells could be embryonic stem cells, bone marrow, or other types of cells, which may be used as pools of candidate cells to select for FGF1-producing cells.

The following examples are for purposes of illustration only and are not intended to limit the scope of the claims which are appended hereto.

EXAMPLE 1

A Transgene Comprising a Portion of the Human FGF1B Promoter and the Immediate Early Gene of the SV40 Genome A. Nucleotides −540 to +31 of human FGF-1B and nucleotides 5171 to 2533 of SV40 immediate early genes were cloned into the SmaI-BamHI sites of pGL2-Basic. The T antigen coding sequence (5177 to 2533) was excised from the pW2 plasmid (Chang L S, Pater M M, Hutchinson N I, di Mayorca G. Transformation by purified early genes of simian virus 40. Virology. 133: 341–353, 1984) provided to us by Dr. L. S. Chang of Department of Pediatrics, Ohio State University. The enhancer sequence commonly known as the 239-bp NcoI-PvuII fragment, extending from nucleotides 37 to 275 of the SV40 genome, is not included in our construct. The enhancer sequence has been shown to dictate the T antigen expression and the concomitant tumor formation in many tissues of the transgenic animals and is excluded to provide for tissue specificity. (Messing A, Chen H Y, Palmiter R D, Brinster R L. Peripheral neuropathies, hepatocellular carcinomas and islet cell adenomas in transgenic mice. Nature 316: 461–463, 1985).

Figure 6:
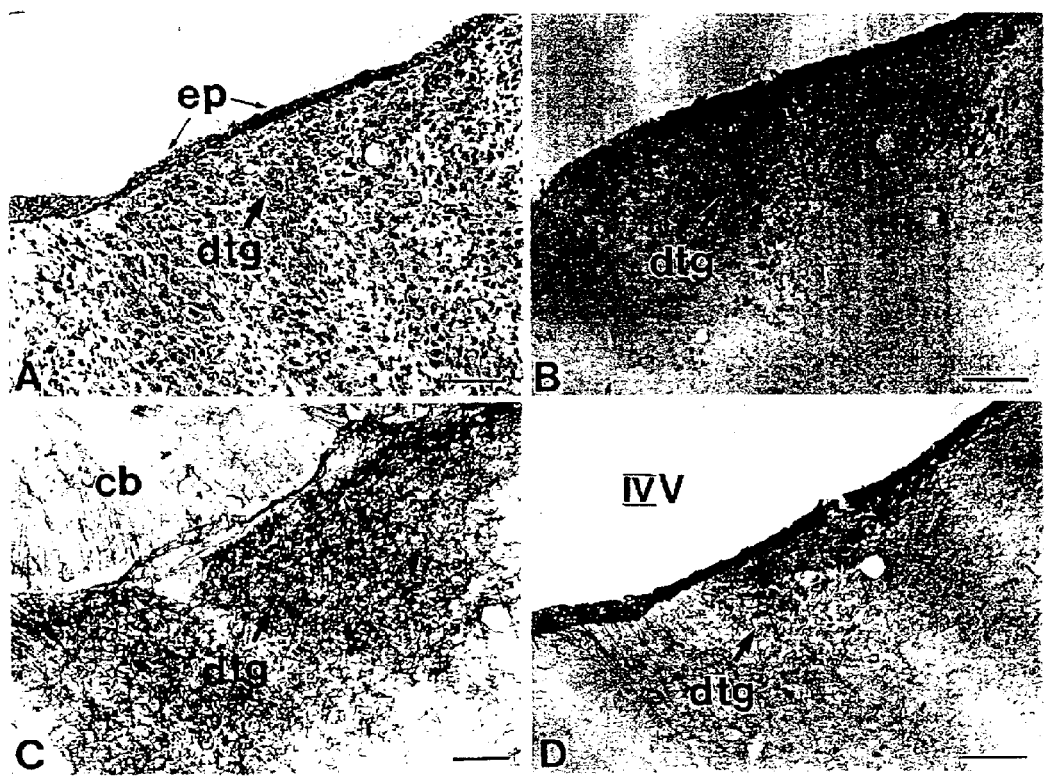
FIG. 6. A cresyl fast violet-stained sagittal section (A) through the midline of a P25 mouse brain (88 line), showing pigmented cells at the site of tumor origin in the pontine raphe/dorsal tegmental nucleus, just below the ependymal membrane at the rostral surface of the fourth ventricle. In adjacent sections, proliferating cells are (B) SV-40T, (C) GFAP and (D) vimentin positive. cb, cerebellar cortex; dtg, dorsal tegmental nucleus; ep, ependymal membrane; IVV, fourth ventricle. Scale bars: 100 $\mu$m.

The sequence of nucleotides −540 to +31 of FGF-1B promoter (SmaI to HindIII), is provided described in publication accession no. (Z14150) and FIG. 6 (Myers, R. L., Payson, R. A., Chotani, M. A., Deaven, L. L., and Chiu, I. -M. (1993). Gene structure and differential expression of acidic fibroblast growth factor mRNA: identification and distribution of four different transcripts. Oncogene 8, 341–349). The sequence of nucleotides 5171 to 2533 (HindIII to HindIII) in the genome is depicted in GenBank Accession No. NC_001669. The sequence of the entire plasmid comprising the resulting transgene is shown in FIG. 10.

EXAMPLE 2

Transgenic Mice Comprising the Transgene of Example 1.

FGF1B promoter (nucleotides −540 to +31) was ligated upstream of the SV40 immediate early gene sequence. The resultant F1B-Tag plasmid DNA (FIG. 1) was linearized at the unique BamHI site and microinjected into zygotes. Embryos were implanted into surrogate mother mice at The Ohio State University Transgenic Facilities. The transgenic mice were identified by PCR analysis using genomic DNA isolated from their tails as templates (data not shown). Those that were positive with a 312-bp amplicon were subjected to Southern blotting analysis to verify the presence of the FIB-Tag transgene.

Figure 2:
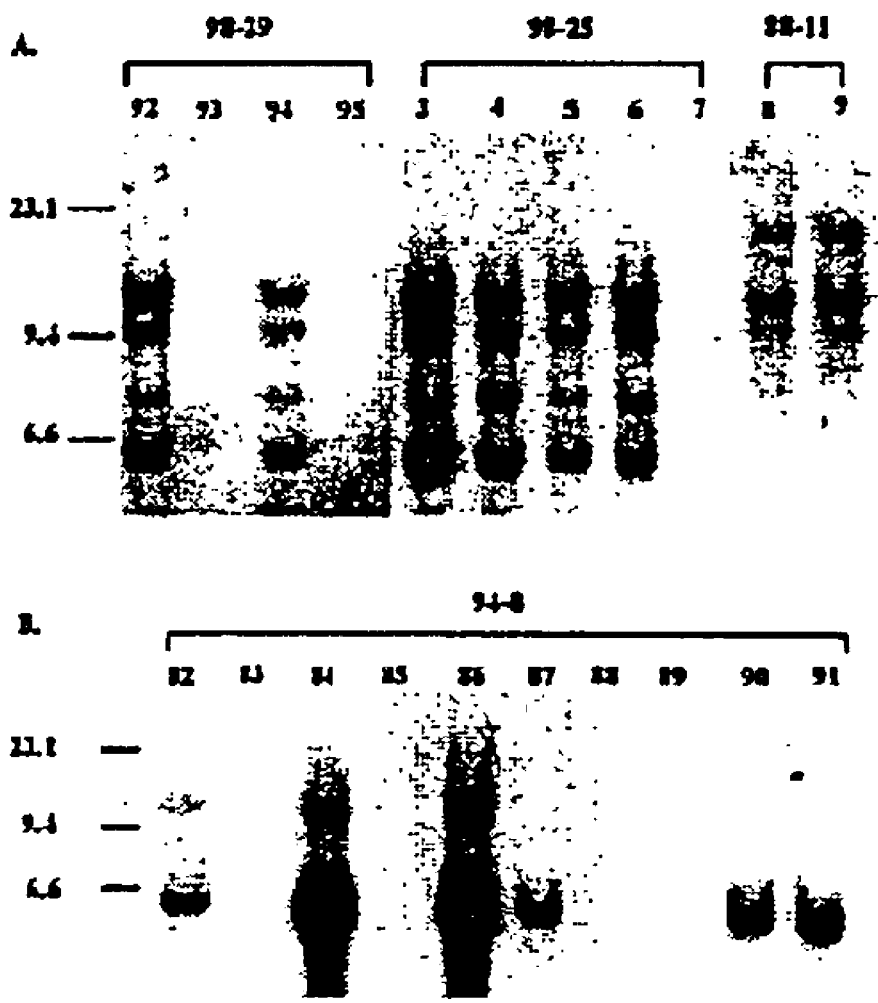
FIG. 2. Southern blots of F1B-TAg transgenic mouse DNA. Mouse-tail DNA was digested with BamHI, separated on an agarose gel, and blotted to a filter. The filter was hybridized to a 1.2-kbp HindIII fragment derived from SV40 immediate early gene sequences. Each of the four lines has a distinct pattern of hybridization, indicating different integration sites of the transgenic DNA. Panel A shows the offspring of mice 98-29, 98-25 and 88-11. Panel B shows the offspring of mouse 94-8. Lambda DNA digested with HindIII was used as a molecular weight marker and the sizes in kbp are indicated on the left of each panel.

Three founder mice (88, 94, and 98) were initially identified and mated. Representative Southern blots of the F2 generation of each of the three families are shown in FIG. 2. The filter was hybridized to a 1.2-kbp HindIII fragment derived from the SV40 immediate early gene region. FIG. 2A shows the offspring of F1 transgenic mice 98-29, 98-25 and 88-11. Each family had a unique pattern of hybridizing bands, indicating a distinct transgenic DNA integration site. In contrast, two different hybridization patterns for offspring of mouse 94-8 were detected (FIG. 2B) Mice 94-8-84 and 94-8-86 showed higher intensity signals than mice 94-8-87, 94-8-90 and 94-8-91, indicating that the former contains a higher copy number of the transgene. Mice with the higher copy number also had an additional band at 10 kbp (FIG. 2B), which helped to identify mouse 94-8-82 as a high-copy number animal. The apparent low intensity of hybridizing bands in this lane was due to the loading of less DNA, which was visualized by staining the gel with ethidium bromide. The results suggest that founder 94 had two non-allelic integration sites (denoted H and L for high- and low-copy number, respectively).

Figure 3:
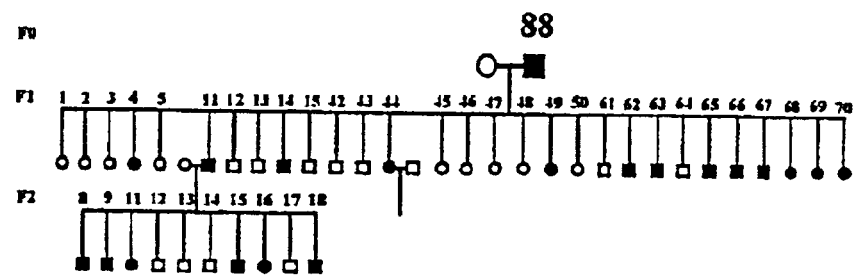
FIG. 3. A pedigree of the four FIB-Tag transgenic lines, 88, 94H, 94L and 98. A partial pedigree analysis is presented to examine the heritability of the phenotype of premature death and brain tumor. Females are indicated by open circles, males by open squares, and transgenic mice by solid circles and squares. The founder 94 contains two non-allelic transgenes. Hatched circles and squares indicate those that inherited the low copy number locus in the 94L line. The mouse 94-8-82 contains only the high copy number locus (94H), while the mouse 94-16 contains only the low copy number locus (94L).
Figure 3:
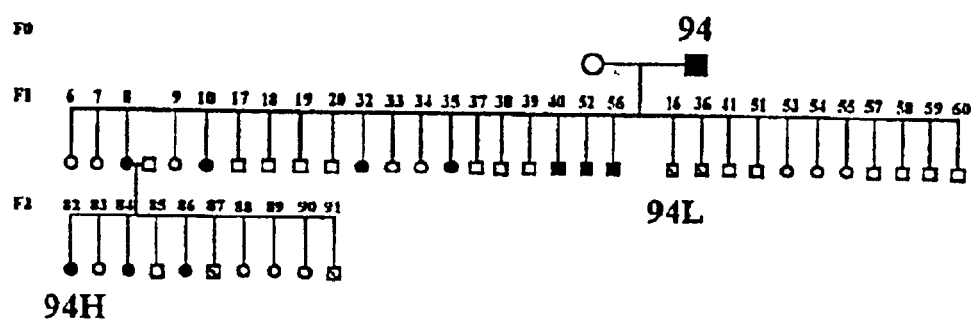
Figure 3:
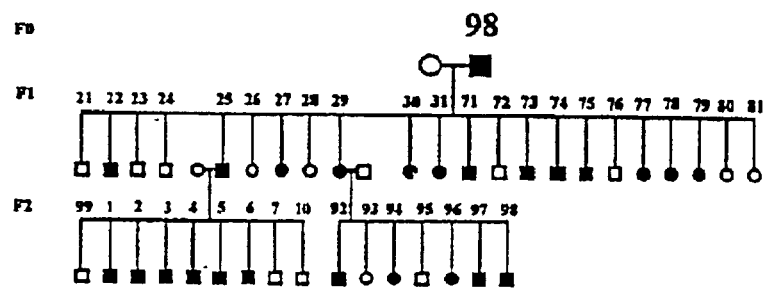

A partial pedigree of each of the three families, showing that the transgene was inherited according to Mendel's law, is depicted in FIG. 3. The transgenic offspring of 94-8 showed the inheritance of either the H or L locus, suggesting that 94-8 inherited both the H and L loci from her founder father. All six transgenic offspring of 94-16, as well as those up to generation F5, inherited only the L locus (data not shown). Similarly, all five transgenic offspring of 94-8-82, as well as those up to the F5 generation, inherited only the H locus (data not shown). Thus, we concluded that the two integration sites in founder 94 have been segregated, and the two lines are referred to as 94H and 94L, respectively (FIG. 3).

The life span of transgenic animals was considerably shorter than that of normal mice of the parent strain. The mean (±standard deviation) survival time across four generations, excluding mice sacrificed for early data points, was 183(±38), 178(±22), 166(±25) and 212(±35) days for 88, 98, 94H and 94L mice, respectively. Older animals appeared hunched and lethargic, and some animals were ataxic.

Although tumors were occasionally observed in other organs, such as the pancreas (Table I), each of the four transgenic lines manifested brain tumors with complete penetrance. Within the central nervous system, the apparent sites of tumor origin were restricted to the brain stem, generally sparing the cerebral cortex, hippocampus, cerebellum and spinal cord. Tumors were comprised of small cells with scanty cytoplasm and regular round to ovoid nuclei that were stained at moderate intensity by cresyl fast violet (FIG.

Figure 4:
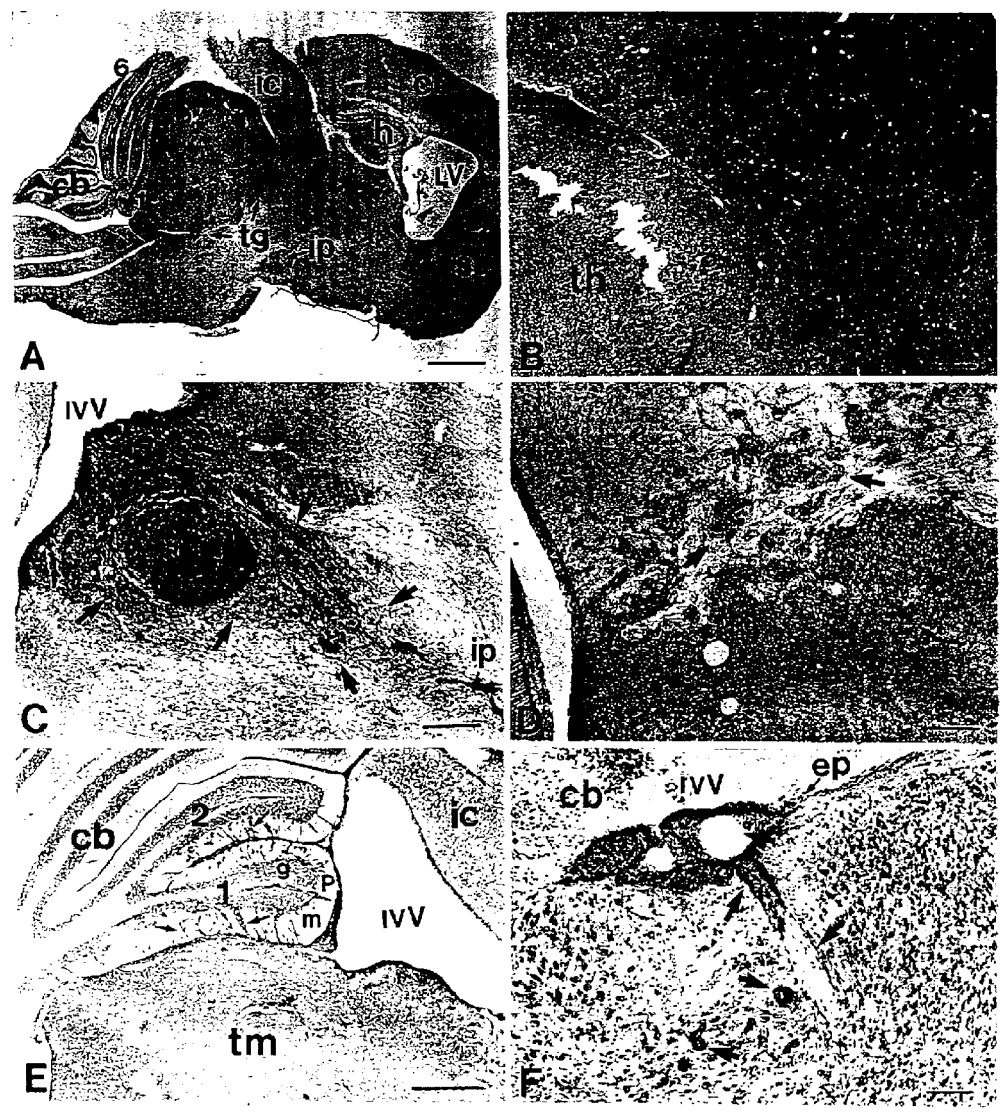
FIG. 4. (A) Cresyl fast violet-stained sagittal section showing a large focal tumor in the caudal pons of a 94H strain mouse at P 147. The cerebellum is flattened and anterior lobules 1–6 are somewhat agranular. (B) A hematoxylin and eosin-stained sagittal section showing multifocal tumors (arrows) in the striatum and thalamus of an adult (P224) 94L strain mouse. (C) A sagittal section from a 98 strain mouse (P 166) labeled with an SV40 T antibody, counter-stained with cresyl fast violet, showing tumor foci distributed in a diagonal stream (arrows), from the tegrnentum to the interpeduncular nucleus. (D) High magnification photomicrograph of a vimentin-stained tumor with smaller cell clusters (arrows) at the periphery. A sagittal section (E) through the cerebellum and pons of a 94H mouse (P 172). This animal is unusual in that cerebellar lobules 1 and 2 are invaded by proliferating cells (small arrows) organized in perpendicular arrays from the pial membrane through the molecular layer. These ectopic cells may be following major blood vessels, which are organized similarly. The main tumor (tm) lies ventral to cerebellar lobule 1. (F) The ependymal membrane (ep) adjacent to the dorsal tegmental nucleus, is thickened by proliferating cells, and is heavily vascularized (arrows). BS, brain stem; cb, cerebellum; ct, cortex; ep, ependymal membrane; g, granule cell layer; h, hippocampus; ic, inferior colliculus; ip, interpeduncular nucleus; m, molecular layer; P, Purkinje cell layer; st, striatum; tg, tegmental area; th, thalamus; tm, tumor; IVV, fourth ventricle; LV, lateral ventricle; 1,6, cerebellar folia 1 through 6. Scale bars: A, E, 500 $\mu$m; B, C, 250 $\mu$m; D, F, 100 $\mu$m.

4A) and hematoxylin (FIG. 4B), clearly delineating the tumors from surrounding tissue. Tumors of different sizes were distributed along myelinated fiber tracts, suggesting that infiltrating tumor cells followed these structures. In strain 88 and 98 mice, foci were entirely restricted to the caudal pontine regions of the brain stem, and appeared to originate in the dorsal tegmental region, at the rostral surface of the fourth ventricle. In general, tumor foci in the 98 strain were distributed over a larger area than those of line 88 animals. As with the 88 and 98 lines, major foci were also concentrated in the tegmental region in adult mice of the 94H and 94L lines (FIG. 4C,D). Additional smaller foci were scattered in a diagonal stream from the pontine central gray into the interpeduncular nucleus at the ventral surface of the brain stem. However, unlike 88 and 98 mice, tumor cells were also present in all subnuclear regions of the thalamus, and in the striatum (caudate, putamen, accumbens), ventral forebrain (olfactory tubercle, amygdala) (FIG. 4A,B), and olfactory bulbs. (data not shown). Foci were distributed differentially in 94L and 94H mice: In 94L animals, tumors in the pontine gray-interpeduncular stream were far smaller and less frequent than in 94H animals, while tumors in the thalamus, striatum, forebrain and olfactory bulbs were more numerous and far larger. Although the degree to which the tumors invaded the brain stem varied across the four lines, within each line the place of origin and final distribution of major foci were highly reproducible across animals. The distribution of CNS tumors in each transgenic line is schematized in FIG. 5, and their frequency is shown in Table II.

Abnormalities were also observed in specific brain regions apparently unaffected by tumor activity. Although the cerebellum was generally spared, it was frequently flattened and lobules 1 through 6 were somewhat agranular (FIG. 4A). This was likely the result of increased cerebellar compression between the enlarging tumor and the cranium, possibly accounting for the ataxia observed in some of the older mice. In one anomalous 94H F3 generation mouse (94-8-82-28), tumor cells, apparently associated with the ependymal lining of the fourth ventricle, extended from the dorsal surface of the medulla into posterior cerebellar folia 1 and 2 (FIG. 4E). These cells infiltrated tangentially through the molecular and Purkinje cell layers into the granule cell layer. In addition, in some animals patches of ependymal lining at the rostral ventricular surface appeared thickened and distorted, extending into the underlying brain tissue accompanied by enlarged blood vessels (FIG. 4F). Clustered tumor cells within the Virchow-Robin spaces and. in the subependymal region suggested that these are highly motile cells that migrate in association with these structures, mimicking the secondary structures of Scherrer. In older mice (P 160 onward), the ventricles were greatly distended and several mice exhibited obstructive hydrocephalus. In several 94H mice, irregularly shaped tangles of ependymal lining were present within the fourth ventricle (data not shown).

Figure 7:
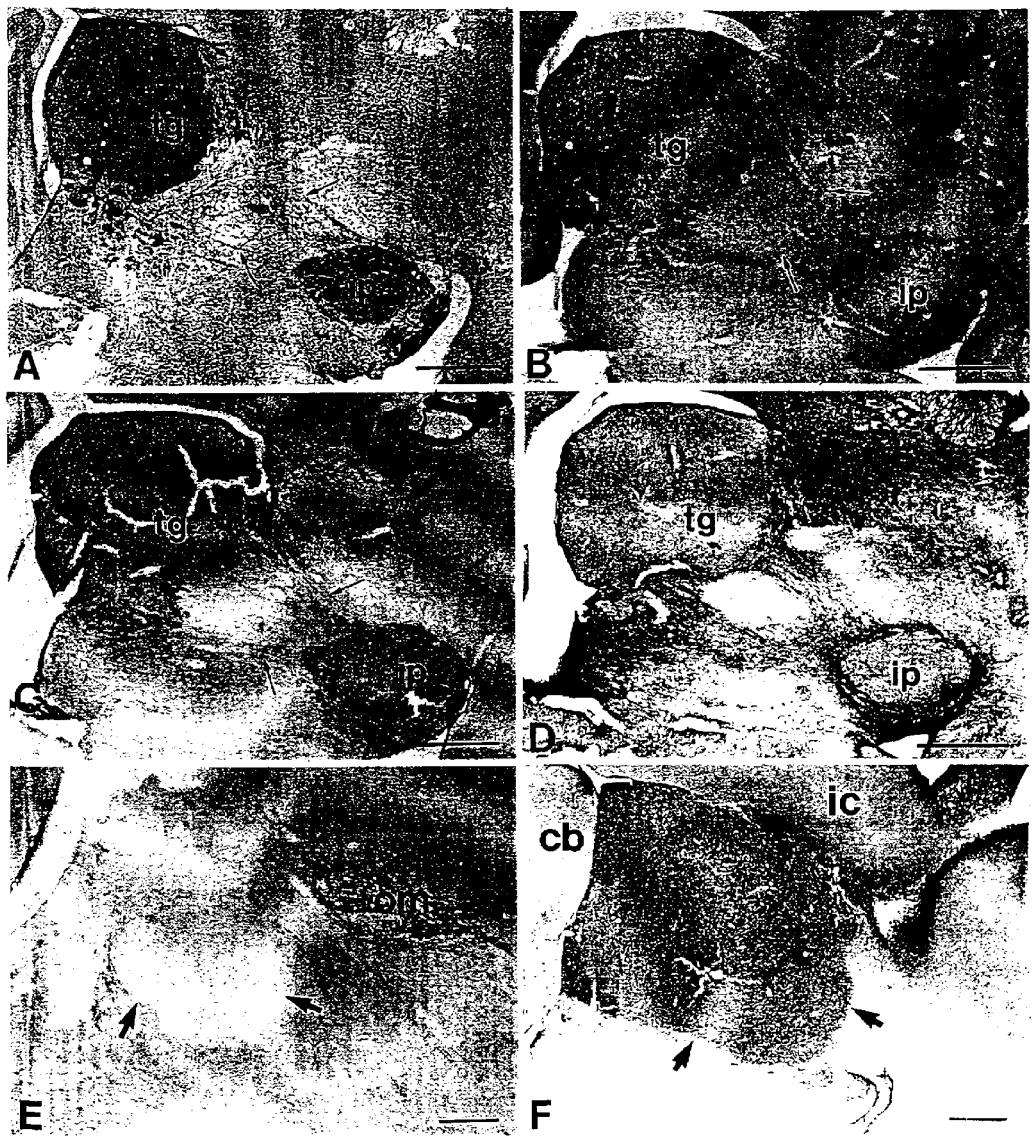
FIG. 7. Sagittal sections through the brain stem of an adult (P200) mouse of the 88 line. (A) A cresyl fast violet-stained section showing a large tumor extending throughout the dorsal and ventral tegmental nuclei (tg) and pontine raphe nucleus, and into the fourth ventricle. A separate tumor is located in the interpeduncular nucleus (ip) at the ventral surface of the brain stem. High levels of punctate PCNA staining are detected throughout the tumor (B); the vimentin antibody is distributed similarly (C). In a mature animal, GFAP staining (D) is present at the periphery of the tumors and throughout tracts (small arrows) joining the two major foci; however, it is largely absent from the body of the tumor. All tumors were FGF1-negative (E) and SV40 positive (F). cb, cerebellar cortex; ic, inferior colliculus; ip, interpeduncular nucleus; om, occulomotor nucleus; tg, tegmental nuclei;. Large arrows in E and F indicate the ventral border of the tumor. Scale bars: A–D 500 $\mu$m; E–F, 250 $\mu$m.

Immunocytochemical markers known to be present in neurons, glia, vascular endothelial cells, tumor cells, and proliferating cells (Table III) were used to identify the location and cell type from which the tumors originated, and the magnitude of the proliferating population. An antibody to the SV40 T antigen identified the smallest cellular aggregates, which at early time points (P26–30) were undetectable using standard histological procedures. In each of the four transgenic lines, scattered small T antigen-positive cells became detectable in the pontine raphe and dorsal tegmental nuclei by postnatal day (P)26 (FIG. 6A,B). By P30, additional small aggregates were present throughout the pontine central gray (sphenoid, and dorsal and ventral tegmental nuclei), radiating rostroventrally and mediolaterally into the pons and medulla. These smaller foci followed the general pathways of the decussation of the superior cerebellar peduncle, the mammillotegmental tract, and associated blood vessels. Tumor foci in P26–P35 mice contained moderate levels of GFAP, and lower levels of vimentin (FIG. 6C,D). As the animals matured, many of the smaller foci became fused into multicellular masses of variable size, spreading from the pontine central gray into the interpeduncular nucleus at the ventral pontine surface (FIG. 7A). Punctate PCNA staining (FIG. 7B), indicating proliferating cells in the GI and S phases of the cell cycle, became increasingly intense. In mature mice, high levels of vimentin were present (FIG. 7C), but GFAP staining was generally absent within the perimeter of all major foci (FIG. 7D), thus reversing the staining pattern observed in the younger animals (Table III). All tumor foci were negative for FGF1 (FIG. 7E), but continued to exhibit high levels of T antigen (FIG. 7F).

Figure 8:
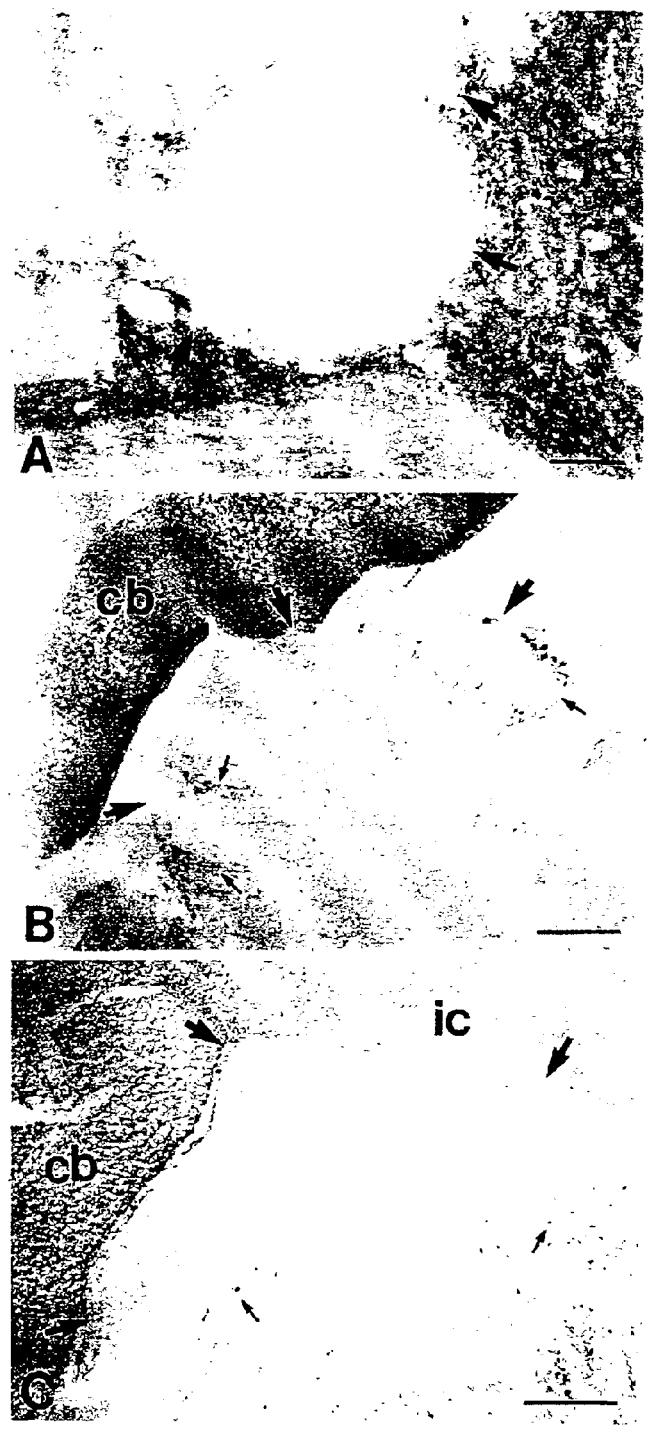
FIG. 8. Sagittal sections through the tegmental region of an adult 88 mouse showing the absence of (A) neuron specific enolase, (B) synaptophysin, and (C) S-100-positive cells within the tumor. cb, cerebellar cortex; ic, inferior colliculus; large arrows indicate the border of the tumor; small arrows in B and C indicate a few remaining labeled cells. Scale bars: A, 100 $\mu$m; B, C, 200 $\mu$m.
Figure 9:
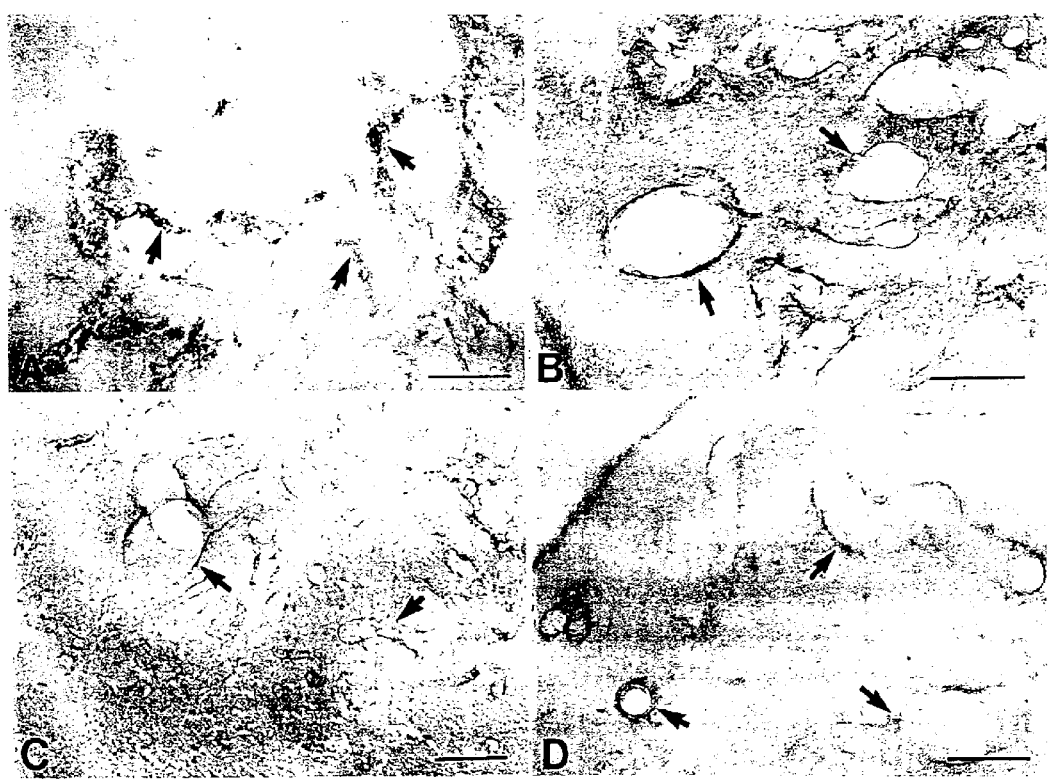
FIG. 9. All major foci are heavily vascularized. Panel (A), vWF-positive cells associated with blood vessels at the tumor periphery. (B) Blood vessels within the tumor lined with vWF-positive cells. Larger blood vessels are also positive for CD31 (C) and VEGF (D). Arrows indicate blood vessels. Scale bars: A, 200 $\mu$m; B, 100 $\mu$m; C, D, 50 $\mu$m.

Neuronal cell markers, including neuron-specific enolase (NSE) and synaptophysin, and a glial cell marker, S-100, although present within their appropriate cell types in areas unaffected by tumor, were either completely undetectable or present only in scattered cells within the tumor boundary, probably in entrapped, non-neoplastic cells (FIG. 8A–C). Enlarged blood vessels, identified by endothelial cell markers CD-31 and von Willebrand factor (Takahashi, K., Mulliken, J. B., Kozakewich, H. P., Rogers, R. A., Folkmnan, J., and Ezekowitz, R. A. (1994) Cellular markers that distinguish the phases of hemangioma during infancy and childhood. J. Clin. Invest. 93, 2357–2364), invaded all larger tumor foci (FIG. 9A–C). For a tumor to expand beyond a prevascular size, it must produce angiogenesis stimulators (Hanahan, D., and Folkman, J. (1996). Patterns and emerging mechanisms of the angiogenic switch during tumorigenesis. Cell 86, 353–364). Vascular endothelial growth factor (VEGF), a potent angiogenic factor (Risau, W. (1997). Mechanisms of angiogenesis. Nature 386, 671–674), is expressed in blood vessels within FIB-Tag tumors (FIG. 9D).

Figure 5:
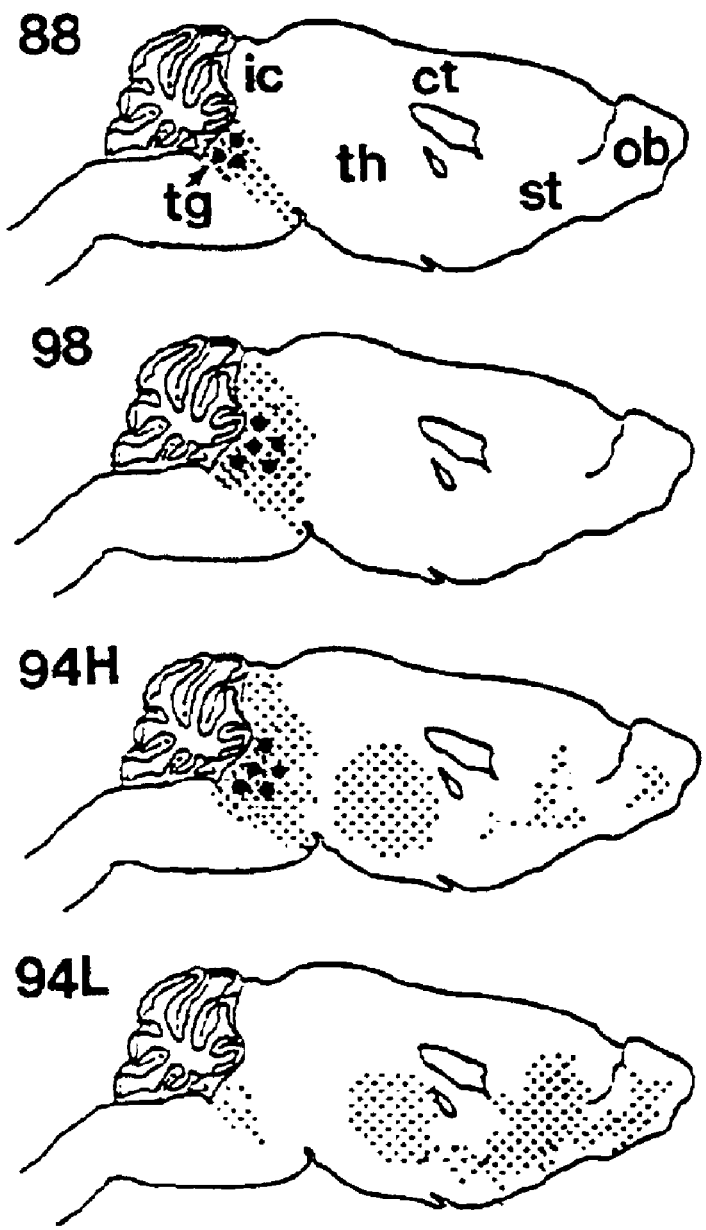
FIG. 5. A schematic of the distribution of brain tumors in 88, 98, 94H and 94L transgenic lines.

We have generated four lines of transgenic mice using the brain-specific FGF-1B promoter to drive the expression of SV40 large T antigen, which manifests its transforming potential through inactivation of two major cellular tumor suppressor proteins, p53 and pRb (Symonds et al., 1994). Each of the transgenic mice developed brain stem tumors of various sizes, most consistently in the caudal pons. Within this region, the location of F1B-Tag tumors was highly reproducible, in that all four lines developed tumors at the anterior surface of the fourth ventricle near the midline, a region known for its susceptibility to tumor formation. Southern blotting analysis showed that the copy numbers of the four transgenic lines ranked as follows: 94H>98>88>94L (FIG. 2). The dosage of the transgene is reflected in the size of the pontine tumors formed in each line. Thus, 94H and 98 exhibited larger tegmental tumors than 88 mice, which, in turn, had more extensive tumors than 94L animals (FIG. 5). Furthermore, the higher copy number also reflected shorter survival time. These results suggest that the amount of T antigen in each of the transgenic lines is directly proportional to the severity of the brain tumor. It is noted that the tumor was more widely spread in the 94H and 94L lines than in the 88 and 98 lines, often extending anteriorly into the thalamus, striatum and olfactory bulbs (FIG. 5). Therefore, the integration sites of the transgene may also contribute to the spatial distribution of the brain tumor.

Histogenesis of the Pontine Tegmental Nuclei

The nervous system evolves from a layer of stratified multipotent stem cells in the primitive neuroectoderm (Davis, A. A., and Temple, S. (1994) A self renewing multipotential stem cell in embryonic rat cerebral cortex. Nature 372, 263–266). Normal cells undergo highly orchestrated developmental processes involving cell proliferation; migration, and differentiation. In each of the four transgenic lines, F1B-Tag tumors originated within the dorsal pons; specifically in the dorsal tegmental and/or pontine raphe nuclei. The histogenesis of these closely associated regions has been described in detail (Taber-Pierce, E. (1966) Histogenesis of the nuclei griseum pontis, corporis pontobulbaris and reticularis tegmenti ponti (Bechterew) in the mouse. J. Comp. Neurol. 126, 219–240). Although a small number of cells in the dorsal tegmental nuclei appear to originate in the rhombic lip, the genesis of the great majority of tegmental precursors occurs on gestation days 12–13 in the ependyma of the fourth ventricle. These primitive cells are located within a limited region of the basal plate, just lateral to the midline, at the level of the pontine flexure. Similarly, neuroblasts giving rise to the pontine raphe, a narrow, midline structure dorsal to, and abutting, the dorsal tegmental nuclei, arise slightly earlier, on gestation days 10 and 11, from the same ventricular region (Taber-Pierce, E. (1966) Histogenesis of the nuclei griseum pontis, corporis pontobulbaris and reticularis tegmenti ponti (Bechterew) in the mouse. J. Comp. Neurol. 126, 219–240). Within 24–48 hours of birth, neuroblasts destined for both regions migrate to their adult position on either side of the midline, ventral to the medial longitudinal fasciculus. Epigenetic influences during any of these embryonic processes may be sufficient to block normal cellular development and lead to the formation of primitive neuroectodermal tumors at a later stage (Yachnis, A. T., Rorke, L. B., and Trojanowski, J. Q. (1994). Cerebellar dysplasia in humans: Development and possible relationship to glial and primitive neuroectodermal tumors of the cerebellar vermis. J. Neuropathol Exp. Neurol. 53:61–71).

The commitment of CNS progenitor cells to neuronal or glial lineage, and the maturation of neurons and glia, are signaled by the coordinated expression of many developmentally regulated proteins (Anderson, D. J. (1999). Lineages and transcription factors in the specification of vertebrate primary sensory neurons. Curr. Opinion. Neurobiol. 9, 517–524). For example, vimentin is expressed in progenitor cells that retain the plasticity to differentiate into cells of neuronal or glial lineage; it is replaced by synaptophysin and neuron-specific enolase in mature neurons, and by GFAP in astrocytes (Pekny, M., Johansson, C. B., Eliasson, C., Stakeberg, J., Wallen, A., Perlmann, T., Lendahl, U., Betsholtz, C., Berthold, C. H., Frisen, J. (1999). Abnormal reaction to central nervous system injury in mice lacking glial fibrillary acidic protein and vimentin. J. Cell Biol. 145, 503–514). Three different intermediate filaments, nestin, vimentin, and GFAP, are found in astrocytes and their precursors. In immature astrocytes, nestin and vimentin are the main intermediate filaments, whereas maturing and adult astrocytes contain vimentin and GFAP, respectively. During reactive gliosis, nestin production is resumed, and vimentin and GFAP expression is upregulated in activated astrocytes (Eng, L. F., and Ghirnikar, R. S. (1994). GFAP and astrogliosis. Brain Pathol. 4, 229–237; Frisen, J., Johansson, C. B., Torok, C., Risling, M., and Lendahl, U. (1995). Rapid, widespread, and longlasting induction of nestin contributes to the generation of glial scar tissue after CNS injury. J. Cell Biol. 131, 453–464).

Comparison with widely used tumor markers suggests that the F1B-Tag tumor falls into the general category of the primitive neuroectodermal tumor (PNET). Our F1B-Tag mice comprises tumors which are at a unique site and at a unique stage of differentiation. The cells of the F1B-Tag tumors do not express any of the neuronal markers tested, including synaptophysin and neuron-specific enolase (FIG. 8). The cells of the F1B-Tag tumors express vimentin, a protein which is absent from an oligodendroglioma or choroid plexus papilloma (Reifenberger, G., Szymas, J., and Wechsler, W. (1987). Differential expression of glial- and neuronal-associated antigens in human tumors of the central and peripheral nervous system. Acta Neuropathol. 74: 105–123). The FIB-Tag tumor is unlikely to be an astrocytoma as the mature tumor does not express GFAP. The cells of the FIB-Tag tumors do not progress along the neuronal lineage to the point of expressing either glial or neuronal markers. It is believed that the cells of the FIB-Tag tumors are prohibited from reaching terminal differentiation, setting the stage for tumorigenesis, and providing a unique in vivo system in which to study the induction and progression of PNETs.

The immunophenotype of the cells of the FIB-Tag tumors is consistent with the tumor being at an early stage of differentiation. Therefore, the present transgenic mice are a valuable tool for the study of tumorigenesis, as well as the replenishment and differentiation of neural stem cells.

Neural Stem Cells and Origin of Tumor Cells

Until recently, it was believed that adult brains were doomed to a constant, steady decline. It appeared that, shortly after birth, neurons lost their ability to grow and cells that died could not be replaced. However, in the past few years, it has been reported that certain kinds of neurons can grow in adult brains (Temple, S., and Alvarez-Buylla, A. (1999). Stem cells in the adult mammalian central nervous system. Curr. Opin. Neurobiol. 9, 135–141). Self-renewing, totipotent embryonic stem cells may provide a virtually unlimited donor source for transplantation (Brustle, O., Jones, K. N., Learish, R. D., Karrarn, K., Choudhary, K., Wiestler, O. D., Duncan, I. D., and McKay, R. D. G. (1999). Embryonic stem cell-derived glial precursors: A source of myelinating transplants. Science 285, 754–756). Recently, two groups have identified glial cells in the dentate gyrus of the hippocampus as a source of proliferating neurons. However, it is not clear whether the glial cells were derived from the ependymal layer (Johansson, C. B., Momma, S., Clarke, D. L., Risling, M., Lendahl, U., and Fris6n, J. (1999). Identification of a neural stem cell in the adult mammalian central nervous system. Cell 96, 25–34) or the subventricular zone (Doetsch, F., Caille, I., Lim, D. A., Garcia-Verdugo, J. M., and Alvarez-Buylla, A. (1999). Subventricular zone astrocytes are neural stem cells in the adult mammalian brain. Cell 97, 703716) of the lateral ventricles. Although these precursor cells were conveniently defined as glial cells because they expressed GFAP, it is quite possible that these GFAP-positive cells were precursors of both glial and neuronal lineages (Barres, B. A. (1999). A new role for glia: Generation of neurons! Cell 97, 667–670). The resolution of this controversy will require identification of additional markers that identify specific precursor cells. Our tumor cells, which lack both GFAP and synaptophysin, are expected to provide a useful source for generating these neural stem cell markers.

EXAMPLE 3

Preparation and Characterization of Tumor Cells Obtained from Mice of Example 2

Brain tumors dissected from 4-month old F1B-Tag mice were triturated with 22-gauge needles and grown in Dulbecco's modified Eagle medium (DMEM) supplemented with 5% fetal calf serum, EGF (10 ng/ml) and FGF1 (10 ng/ml) as described (1a). Aliquots of fresh growth factor-containing medium were added every other day. Cells from a second or third passage were used for differentiation studies. The results showed that F1B-Tag tumor cells could differentiate into GFAP-expressing astrocytes when FGF1 and EGF were withdrawn from medium and LIF (10 ng/ml) was added to medium for 6 days. These GFAP-expressing astrocytes are most likely derived from the F1B-Tag tumor as they continued to express FGF1 and T antigen. When the F1B-Tag cells were cultured in the presence of (PDGF; 10 ng/ml), 75 to 95% of the cells were positive for the immunostaining of synaptophysin. In the presence of thyroid hormone T3 (10 mM), 25% to 45% of the cells became positive for galactocerebroside (Ga1C), a marker for oligodendrocytes. The results showed that the F1B-Tag cells are capable of differentiating into all three neural progeny lineages. The fact that these tumor cells can differentiate into astrocytes, neurons, and oligodendrocytes is evidence that the F1B-Tag tumor cells are pluripotent neural stem cells.

Reference

Alan, K. Y., Frostholm, A., Hackshaw, K. V., Evans, J. E., Rotter, A., and Chiu, I.-M. (1996). Characterization of the 1B promoter of fibroblast growth factor 1 and its expression in the adult and developing mouse brain. J. Biol. Chem. 271, 30263–30271.

Anderson, D. J. (1999). Lineages and transcription factors in the specification of vertebrate primary sensory neurons. Curr. Opinion. Neurobiol. 9, 517–524.

Barres, B. A. (1999). A new role for glia: Generation of neurons! Cell 97, 667–670.

Bergers, G., Javaherian, K., Lo, K. -M., Folkrnan, J., Hanahan, D. (1999). Effects of angiogenesis inhibitors on multistage carcinogenesis in mice. Science 284, 808–812.

Black, D. L. (1998). Splicing in the inner ear: a familiar tune, but what are the instruments? Neuron 20, 165–168.

Brustle, O., Jones, K. N., Learish, R. D., Karrarn, K., Choudhary, K., Wiestler, O. D., Duncan, I. D., and McKay, R. D. G. (1999). Embryonic stem cell-derived glial precursors: A source of myelinating transplants. Science 285, 754–756.

Chiu, I. -M., Wang, W. -P., Lehtoma, K. (1990). Alternative splicing generates two forms of mRNA coding for human heparin binding growth factor 1. Oncogene 5, 755–762.

Cho, J. Y., Xing, S., Liu, X., Buckwalter, T. L. F., Hwa, L., Sferra, T. J., Chiu, I. -M. and Jhiang, S. M. (2000) Expression and activity of human Nell" symporter in human glioma cells by adenovirus-mediated gene delivery. Human Gene Therapy, In press.

Chotani, M. A., and Chiu, I. -M. (1997). Differential regulation of human fibroblast growth factor 1 transcripts provides a distinct mechanism of cell-specific growth factor expression. Cell Growth Differ. 8, 9999–10013.

Davis, A. A., and Temple, S. (1994) A self renewing multipotential stem cell in embryonic rat cerebral cortex. Nature 372, 263–266.

Doetsch, F., Caille, I., Lim, D. A., Garcia-Verdugo, J. M., and Alvarez-Buylla, A. (1999). Subventricular zone astrocytes are neural stem cells in the adult mammalian brain. Cell 97, 703716.

Eckenstein, F. P., Kuzis, K., Nishi, R., Woodward, W. R., Meshul, C., Sherman, L., and Ciment, G. (1994). Cellular distribution, subcellular localization and possible functions of basic and acidic fibroblast growth factors. Biochem Pharmacol. 47, 103–110.

Eng, L. F., and Ghirnikar, R. S. (1994). GFAP and astrogliosis. Brain Pathol. 4, 229–237.

Fearon, E. R., and Vogelstein, B. (1990). A genetic model for colorectal tumorigenesis. Cell 61, 759–767.

Frisen, J., Johansson, C. B., Torok, C., Risling, M., and Lendahl, U. (1995). Rapid, widespread, and longlasting induction of nestin contributes to the generation of glial scar tissue after CNS injury. J. Cell Biol. 131, 453–464.

Hanahan, D. (1985). Heritable formation of pancreatic (3-cell tumours in transgenic mice expressing recombinant insulin/simian virus 40 oncogenes. Nature 315. 115–122.

Hanahan, D., and Folkman, J. (1996). Patterns and emerging mechanisms of the angiogenic switch during tumorigenesis. Cell 86, 353–364.

Johansson, C. B., Momma, S., Clarke, D. L., Risling, M., Lendahl, U., and Fris6n, J. (1999). Identification of a neural stem cell in the adult mammalian central nervous system. Cell 96, 25–34.

Khan, J., Bittner, M. L., Chen, Y., Meltzer, P. S., and Trent, J. M. (1999). DNA microarray technology: the anticipated impact on the study of human disease. Biochim. Biophys. Acta 1423: M17–M28.

Liu, Y., Ray, S. K., Yang, X. -Q., Luntz-Leybman, V., and Chiu, I. -M. (1998) A splice variant of E2–2 basic helix-loop-helix protein represses the brain-specific fibroblast growth factor 1 promoter through the binding to an imperfect E-box. J. Biol. Chem. 273, 19269–19276.

Madiai, F., Hackshaw, K. V., and Chiu, I. -M. (1999) Characterization of the entire transcription unit of the mouse fibroblast growth factor 1 (FGF-1) Gene. J. Biol. Chem. 274, 11937–11944.

McKeehan, W. L., Wang, F., Kan, M. (1998). The heparan sulfate-fibroblast growth factor family: diversity of structure and function. Prog. Nucleic Acid Res. Mol. Biol. 59, 135–76.

Mehta, V. B., Connors, L., Fang, H. -C., Chiu, I. -M. (1998) Fibroblast variants nonresponsive to fibroblast growth factor 1 are defective in its nuclear translocation. J. Biol. Chem. 273, 4197–4205.

Messing, A., Chen H. Y., Palmiter, R. D., and Brinster, R. L. (1985). Peripheral neuropathies, hepatocellular carcinomas and islet cell adenomas in transgenic. mice. Nature 316, 461–463.

Mignatti, P., Morimoto, T., Rifkin, D. B. (1992) Basic fibroblast growth factor, a protein devoid of secretory signal sequence, is released by cells via a pathway independent of the endoplasmic reticulum-Golgi complex. J. Cell. Physiol. 151, 81–93.

Myers, R. L., Payson, R. A., Chotani, M. A., Deaven, L. L., and Chiu, I. -M. (1993). Gene structure and differential expression of acidic fibroblast growth factor mRNA: identification and distribution of four different transcripts. Oncogene 8, 341–349.

Myers, R. L., Chedid, M., Tronick, S. R., and Chiu, I. -M. (1995a). Different fibroblast growth factor 1 (FGF-1) transcripts in neural tissues, glioblastomas, and kidney derived cell lines. Oncogene 11, 785–789.

Myers, R. L., Ray, S. K., Eldridge, R., Chotani, M. A., and Chiu, I. -M. (1995b). Functional characterization of the brain-specific FGF-1 promoter, FGF-1.B. J. Biol. Chem. 270, 8257–8266.

Ornitz, D. M., Xu, J., Colvin, J. S., McEwen, D. G., MacArthur, C. A., Coulier, F., Gao, G., and Goldfarb, M. (1996) Receptor specificity of the fibroblast growth factor family. J. Biol. Chem. 271, 15292–15297.

Omitz, D. M. (2000). FGFs, heparan sulfate and FGFRs: complex interactions essential for development. Bioessays 22,108–112.

Palmiter, R. D., Chen, H. Y., Messing A., and Brinster, R. L. (1985). SV40 enhancer and large T antigen are instrumental in development of choroid plexus tumours in transgenic mice. Nature 316, 457–460.

Pekny, M., Johansson, C. B., Eliasson, C., Stakeberg, J., Wallen, A., Perlmann, T., Lendahl, U., Betsholtz, C., Berthold, C. H., Frisen, J. (1999). Abnormal reaction to central nervous system injury in mice lacking glial fibrillary acidic protein and vimentin. J. Cell Biol. 145, 503–514.

Ray, S. K., Yang, X. -Q., and Chiu, I. -M. (1997). Transcriptional activation of fibroblast growth factor 1.B promoter is mediated through an 18-base pair cis-acting element. J. Biol. Chem. 272, 7546–7555.

Reifenberger, G., Szymas, J., and Wechsler, W. (1987). Differential expression of glial- and neuronal-associated antigens in human tumors of the central and peripheral nervous system. Acta Neuropathol. 74: 105–123.

Risau, W. (1997). Mechanisms of angiogenesis. Nature 386, 671–674.

Symonds, H., Krall L., Remington, L., Saenz-Robles, M., Lowe, S., Jacks, T., and van Dyke T. (1994). P53-dependent apoptosis suppresses tumor growth and progression in vivo. Cell 78, 703–711.

Taber-Pierce, E. (1966) Histogenesis of the nuclei griseum pontis, corporis pontobulbaris and reticularis tegmenti ponti (Bechterew) in the mouse. J. Comp. Neurol. 126, 219–240.

Takahashi, K., Mulliken, J. B., Kozakewich, H. P., Rogers, R. A., Folkman, J., and Ezekowitz, R. A. (1994) Cellular markers that distinguish the phases of hemangioma during infancy and childhood. J. Clin. Invest. 93, 2357–2364.

Tarantini, F., LaVallee, T., Jackson, A., Gamble, S., Carreira, C. M., Garfinkel, S., Burgess, W. H., and Maciag, T. (1998). The extravesicular domain of synaptotagmin-1 is released with the latent fibroblast growth factor-1 homodimer in response to heat shock. J. Biol. Chem. 273, 22209–22216.

Temple, S., and Alvarez-Buylla, A. (1999). Stem cells in the adult mammalian central nervous system. Curr. Opin. Neurobiol. 9, 135–141.

Tooze, J. (1981) Molecular Biology of Tumor Viruses Pt. 2, ed. (Cold Spring Harbor Laboratory, Cold Spring Harbor, N.Y.).

Yachnis, A. T., Rorke, L. B., and Trojanowski, J. Q. (1994). Cerebellar dysplasia in humans: Development and possible relationship to glial and primitive neuroectodermal tumors of the cerebellar vermis. J. Neuropathol Exp. Neurol. 53:61–71.

What is claimed is:

1. A DNA construct comprising a human FGF1B promoter as set forth in nucleotide 43 to nucleotide 550 of SEQ ID NO: 2 operably linked to a nucleotide sequence encoding the SV40 large T antigen.

2. A DNA construct comprising a human FGF1B promoter as set forth in nucleotide 10 to nucleotide 580 of SEQ ID NO: 2 operably linked to a nucleotide sequence encoding the SV40 large T antigen.

3. The DNA construct of claim 1 wherein the SV40 large T antigen encoding sequence comprises an intron within said sequence.

4. A DNA construct for providing neural stem cells, said construct comprising the mouse FGF1B promoter operably linked to a sequence encoding the SV40 large T antigen, wherein the sequence of the mouse FGF1B promoter is set forth in SEQ ID NO. 3.

5. A DNA construct consisting of a human FGF1B promoter as set forth in nucleotide 43 to nucleotide 550 of SEQ ID NO: 2 operably linked to a nucleotide sequence encoding the SV40 large T antigen.

6. A DNA construct consisting of a human FGF1B promoter as set forth in nucleotide 10 to nucleotide 580 of SEQ ID NO: 2 operably linked to a nucleotide sequence encoding the SV40 large T antigen.

* * * * *